(12) United States Patent
Van Berkel-Wijnen

(10) Patent No.: US 10,736,579 B2
(45) Date of Patent: Aug. 11, 2020

(54) BABY TRACKER

(71) Applicant: N.V. NUTRICIA, Zoetermeer (NL)

(72) Inventor: Elzemiek Beatrix Maria Van Berkel-Wijnen, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 97 days.

(21) Appl. No.: 16/060,893

(22) PCT Filed: Dec. 9, 2016

(86) PCT No.: PCT/NL2016/050859
§ 371 (c)(1),
(2) Date: Jun. 8, 2018

(87) PCT Pub. No.: WO2017/099598
PCT Pub. Date: Jun. 15, 2017

(65) Prior Publication Data
US 2018/0360393 A1  Dec. 20, 2018

(30) Foreign Application Priority Data
Dec. 11, 2015  (WO) ................ PCT/NL2015/050858

(51) Int. Cl.
*A61B 5/00* (2006.01)
*G01G 19/44* (2006.01)
(Continued)

(52) U.S. Cl.
CPC .......... *A61B 5/7275* (2013.01); *A61B 5/0077* (2013.01); *A61B 5/1072* (2013.01);
(Continued)

(58) Field of Classification Search
CPC ... A61B 5/7275; A61B 5/1079; A61B 5/1072; A61B 5/0077; A61B 2503/04; G01G 19/50; G01G 19/445; G01G 23/3742
See application file for complete search history.

(56) References Cited

U.S. PATENT DOCUMENTS

| 9,569,948 B1 * | 2/2017 | Platt ...................... G08B 21/24 |
| 2010/0051353 A1 * | 3/2010 | Swan ..................... G01G 19/50 |
| | | 177/25.13 |

(Continued)

FOREIGN PATENT DOCUMENTS

CN  103743458 A  4/2014

OTHER PUBLICATIONS

Withings Smart Kid Scale review (Year: 2016).*
(Continued)

*Primary Examiner* — Nizar N Sivji
(74) *Attorney, Agent, or Firm* — Foley & Lardner LLP

(57) ABSTRACT

The invention provides a system (100a) for tracking infant development, the system comprising: —a portable device (101) including a camera and a processing unit, and —a weighing scale (102), preferably comprising a wireless transceiver; wherein the weighing scale is configured to measure the weight of an infant and to transmit the measured weight information to the portable device; and wherein the portable device is configured to —capture (401) an image of the infant; —combine the received weight information and information derived from the image of the infant to obtain (404) infant development statistics; and —store (403) the image and the obtained infant development statistics in a storage; wherein the information derived from the image includes at least one of the height of the infant and the head circumference of the infant. The invention further provides a portable device, a weighing scale, and a computer readable medium.

24 Claims, 5 Drawing Sheets

(51) Int. Cl.
*G01G 23/37* (2006.01)
*A61B 5/107* (2006.01)
*G01G 19/50* (2006.01)

(52) U.S. Cl.
CPC ......... *A61B 5/1079* (2013.01); *G01G 19/445* (2013.01); *G01G 19/50* (2013.01); *G01G 23/3742* (2013.01); *A61B 2503/04* (2013.01)

(56) References Cited

U.S. PATENT DOCUMENTS

| | | | |
|---|---|---|---|
| 2013/0233627 A1* | 9/2013 | Vidal | G01G 19/414 177/25.13 |
| 2015/0164349 A1* | 6/2015 | Gopalakrishnan | A61B 5/746 600/508 |

OTHER PUBLICATIONS

The smart scale will track your baby's growth (Year: 2016).*

Withings Smart Baby Scale to track weight and height on your phone (Year: 2012).*

B.M.C. Silva, et al., "Mobile-health: A review of current state in 2015", Journal of Biomedical Informatics, Aug. 1, 2015, 56:265-272.

S.K. Vashist, et al., "Commercial Smartphone-Based Devices and Smart Applications for Personalized Healthcare Monitoring and Management", Diagnostics, Aug. 18, 2014, 4(3):104-128.

Withings, "Smart Kid Scale", <http://eirberg.is/sites/eirberg.is/files/Skjalasafn/Adrar_upplysingar/WIT-WS40.pdf>, Dec. 21, 2012, 2 pages.

S. Laotrakunchai, et al., "Measurement of Size and Distance of Objects Using Mobile Devices", 2013 International Conference on Signal-Image Technology & Internet-Based Systems (SITIS), IEEE, Kyoto, Dec. 2, 2013, pp. 156-161.

International Search Report issued in PCT/NL2016/050859, dated Feb. 13, 2017, 10 pages.

International Preliminary Report on Patentability issued in PCT/NL2016/050859, dated Dec. 7, 2017, 16 pages.

* cited by examiner

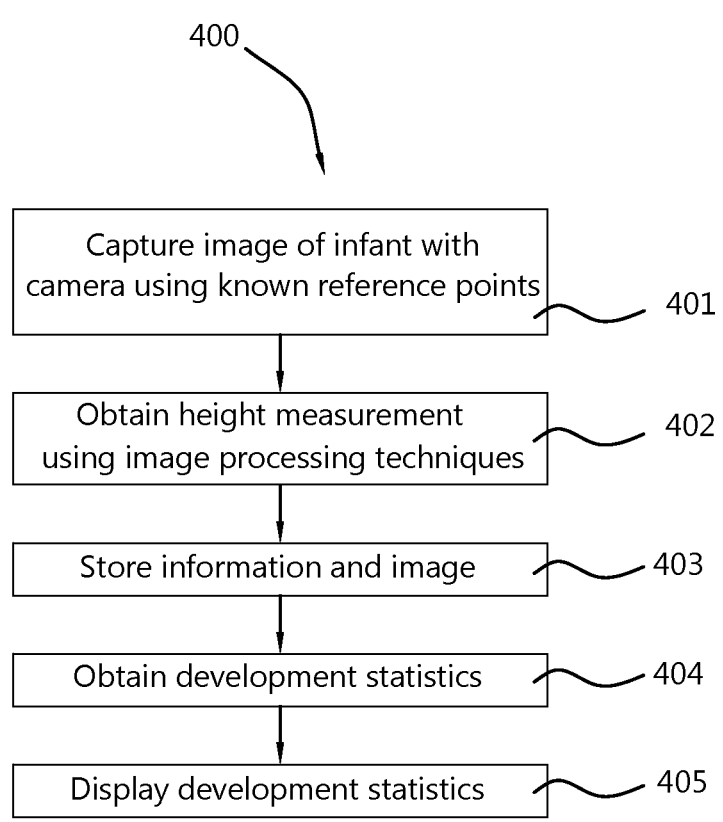

BABY TRACKER

CROSS-REFERENCE TO RELATED APPLICATIONS

This application is the National Phase of International Patent Application No. PCT/NL2016/050859, filed Dec. 9, 2016, which claims priority to International Patent Application No. PCT/NL2015/050858, filed Dec. 11, 2015. The contents of these applications are herein incorporated by reference in their entirety.

FIELD OF THE INVENTION

The invention relates to a system for tracking infant development by using infant weight information provided by measuring devices such as a weighing scale and information derived from a camera image of the infant captured with a portable device.

BACKGROUND OF THE INVENTION

When having the responsibility of taking care of a baby, all precautions seem to not be enough to have the certainty that the baby is all right.

For this reason, every day there are new devices that facilitate the task of taking care of a baby, such as baby monitors to control the baby while not in the same room or while the baby is sleeping.

Specially during its first months, the development of the baby is closely monitored. Frequent questions of parents are: Is my baby developing as it should? Is it developing too fast? Too slow? Are the environment conditions safe for the baby?

It frequently happens that parents visit the paediatrician or healthcare provider (HCP) more than necessary, because of their concerns about their baby's development or condition: the baby eats too much or barely eats, the baby seems to be growing slowly . . . .

It would be desirable that there was a system where parents and caretakers could keep track of the development of their babies in real time, without having to wait until the corresponding visit to the paediatrician, a system that would provide ease of mind to the parents and caretakers, and also provide an indication in case the baby is not developing as expected.

Nowadays, with the habit of people carrying their smartphones, tablet computers or other portable devices with them continuously, there is an effort to provide mobile applications (apps) to be executed by these portable devices that can make normal life tasks easier for the users.

Furthermore, the procedure of taking photos of the baby in order to see its development is a common practice for parents, by means of which they can approximately see how the baby is growing. This does however not provide accurate information, and there is a need for a system using this common tendency of parents of using visual information to track the development of their babies. It would allow that parents and caretakers could use their smartphones, tablet computers or other portable devices to accurately monitor the development of their babies and to solve some of their concerns without having to visit the paediatrician more than necessary.

Therefore, there is a need for a system that allows parents and caretakers to track the development of their baby, in an easy manner via a portable device.

SUMMARY OF THE INVENTION

The invention provides a system for providing infant development information that can be easily monitored using the current portable device technology. The baby's evolution or development can be monitored.

The invention provides a system for tracking infant development, the system comprising a portable device including a camera and a processing unit; and a weighing scale, preferably comprising a wireless transceiver; wherein the weighing scale is configured to measure the weight of an infant and to transmit the measured weight information to the portable device; and wherein the portable device is configured to capture an image of the infant; combine the received weight information and information derived from the image of the infant to obtain infant development statistics; and store the image and the obtained infant development statistics in a storage, wherein the information derived from the image includes at least one of the height of the infant and the head circumference of the infant.

The image and statistics data are stored in a storage. The storage can be provided in the portable device. Alternatively or additionally, the storage is provided on a server connected via a network such as the Internet (e.g. cloud storage). The storage may be a cumulative storage, where data is added with each new measurement. The storage thus includes details of all previous measurements. Smart algorithms can, in real-time or offline, mine this storage to derive further development statistics, such as growth rate, growth spurs, etc.

In the following description, the portable device, which may be a mobile communication device such as a smartphone, may also be referred to as mobile terminal, portable terminal, mobile phone or only phone. However, the invention may also be applied to other types of portable devices such as tablet computers.

The invention therefore provides a system wherein the portable device receives for example via a Bluetooth connection, weight information of the infant from the weighing scale. A processor of the portable device is running an app that is configured to capture an image of the infant, and from the information provided by said image and the weight information received from the weighing scale, development statistics are calculated, stored and represented in a display to the user.

This advantageously allows parents to monitor the development of their babies, by keeping track of the development information obtained. When the infant is developing normally, its development is tracked on a regular basis by a healthcare provider (HCP) but with relative long time periods wherein no HCP takes any measurements of the infant. The present invention allows for more frequent, intermittent taking of reliable measurements without relying on HCPs or other third parties for that. Also, the parent now has more control over information on the development of one's own infant and can visualize its development when desired.

The present invention further advantageously allows parents to take measurements of the infant in an environment that is known and comforting to the baby, in particular in a domestic environment such as at home, at the home of close family or other places that the baby may visit frequently such as a day care centre. In this scenario, the baby feels at ease in its natural environment and this has an impact on the mobility and behavior of the baby. The baby feels relaxed and it does not move nervously, therefore allowing for more accurate measurements, reducing the chance of errors. The taking of measurements using the system of the present invention is thus less upsetting or disturbing for the infant since it takes place in a manner that is largely unnoticed by the infant.

When the developmental statistics are calculated using shape recognition, the present invention has the advantage of allowing the baby to be in any position, without it interfering with the accurate extraction of the information. This simplifies the task to the parent, who needs to make less of an effort to keep the baby in an uncomfortable position.

In an embodiment according the invention, the infant development statistics, in particular physical or growth development statistics of an individual infant, include information of at least one of height, femur length, head circumference, the abdominal perimeter and weight of the infant. This information is used to obtain detailed and accurate developmental statistics. Advantageously, the parent does not need to hold down the legs of the infant to accurately and reliably take said measurements if they are based on shape recognition instead of the height of the baby.

In an embodiment according the invention, the system is intended, programmed or adapted to be able to differentiate between individual siblings. Such programming or adaptation includes the option of manually entering and assigning names of siblings to the information as taken from the respective individual infant. In case there is a substantial difference in size of the siblings, the system is programmed to correctly assign the developmental measurements to the individual infant.

In an embodiment according the invention, the portable device and the weighing scale communicate via a wired (e.g. USB cable) or, preferably, wireless link, such as a Bluetooth link. In the following description, Bluetooth will be used as an example. However, it is possible to use other wired or wireless connections, such as WiFi.

The weighing scale may thus be provided with a Bluetooth transceiver, by means of which it transmits the weight information to a receiving device with which it has a connection link. Bluetooth transmission is an efficient communication mechanism for this type of systems, because it does not have high power requirements. Also, its performance is better with short distances, which is the preferable situation of the present case, since the parent or caretaker will likely be close to the infant when receiving the information from the weighing scale. The Bluetooth technology is also advantageous for this system because the amount of information that has to be transmitted is small.

In an embodiment according the invention, the infant development statistics are displayed on a display of the portable device in the form of a development graph. The app includes a user interface that allows the user to easily manage the different functionalities, among which a graphical representation of the development statistics, such as in a growth graph or development graph, provides a rapid and clear idea of how the baby is developing in comparison with expected patterns. These expected values can be stored in the portable device.

In an embodiment according the invention, the portable device is further configured to receive measuring information from other devices. By using a Bluetooth connection or other similar transmission mechanism, the portable device can establish a connection with other devices that can provide measuring information, and receive more information that can be used to obtain more accurate development statistics. In this way, additional information could be received. All the information received by the portable device from the different measuring devices is used to obtain the development statistics of the baby.

In an embodiment according the invention, the portable device's operating system is one of iOS and Android.

In an embodiment according the invention, the portable device is further configured to transmit the images and the infant development statistics to social media services servers such as Facebook, Twitter, Instagram, and WhatsApp. The portable device may also share the development statistics with a health database shared with the baby's healthcare provider (HCP), so that if there is an indication given for need for special care, the portable device can warn the user to contact the HCP, who will then have quick access to the relevant information to allow faster decision making on the next steps. Alternatively, after a connection has been established with a health database of the HCP, the HCP can warn the parents that some parameters are not within the expected values.

In an embodiment according the invention, the measured information is sent to the portable device automatically every time a measurement is performed.

In an embodiment according the invention, the measured information is sent to the portable device when a request from the portable device is received.

In an embodiment according the invention, the weighing scale with the wireless transmitter is included in an infant changing mat. This advantageously provides a soft and comfortable area where the baby can be lying, and the weight information can easily be obtained.

In an embodiment according the invention, a warning is activated in the portable device if any of the indicators or patterns obtained in the development statistics are outside the expected values or ranges. These expected values might be stored in the portable device, and therefore the app activates a warning message or notification using information of the portable terminal. These expected values might also be stored in the shared health database, and therefore if the information is shared from the portable device to this database, the database will send the warning message or notification, that will be managed by the app. The expected values or ranges are based on growth charts that have been constructed by observing the growth of large numbers of normally developing children over time. The indicators or patterns of the individual infant can be compared to the expected parameters of infants of the same age and/or gender to determine whether the child is growing appropriately. The expected values or ranges are thus preferably based on gender, ethnicity and/or nationality or most preferably any combination thereof to allow the most appropriate comparison to be made.

In an embodiment according the invention, the indicators or patterns are used to predict the expected adult height and weight of the individual child because, in general, children maintain a fairly constant growth curve.

In an embodiment according the invention, the development of the infant is tracked for a period of 24 months, preferably 12 months. The tracking of the development of the infant preferably starts at birth or at least within the first days or weeks after birth.

In an alternative embodiment, the development of the infant is tracked until the infant has reached a height of about 1 meter and 20 centimetres, preferably until about 1 meter. The need to track the development of the human subject is lower after the indicated height or age has been reached since the developmental changes that can be observed and measured are not that pronounced anymore.

The invention further provides a portable device comprising a camera for capturing images, a processing unit for processing information; wherein the portable device is configured to capture at least one image of an infant, obtain infant development statistics with information derived from the at least one image, and store the image and the infant development statistics in a storage; wherein the information derived from the image includes at least one of the height of the infant and the head circumference of the infant.

The invention further provides a weighing scale comprising a transceiver, preferably a wireless transceiver for communicating with the portable device, the weighing scale being configured to measure the weight of an infant, send the measured weight information to the portable device so that the portable device can use it to obtain infant development statistics.

The invention further provides an infant changing mat used for changing diapers to an infant, the changing mat comprising the weighing scale.

The invention further provides computer readable medium comprising computer program instructions which, when executed on a portable device, cause said device to behave as the abovementioned portable device.

Additional aspects are disclosed in the following description and in the dependent claims.

BRIEF DESCRIPTION OF THE FIGURES

On the attached drawing sheets:

FIG. 4 illustrates a process for tracking infant development statistics according to an embodiment of the present invention.

DETAILED DESCRIPTION

Figure 1A:
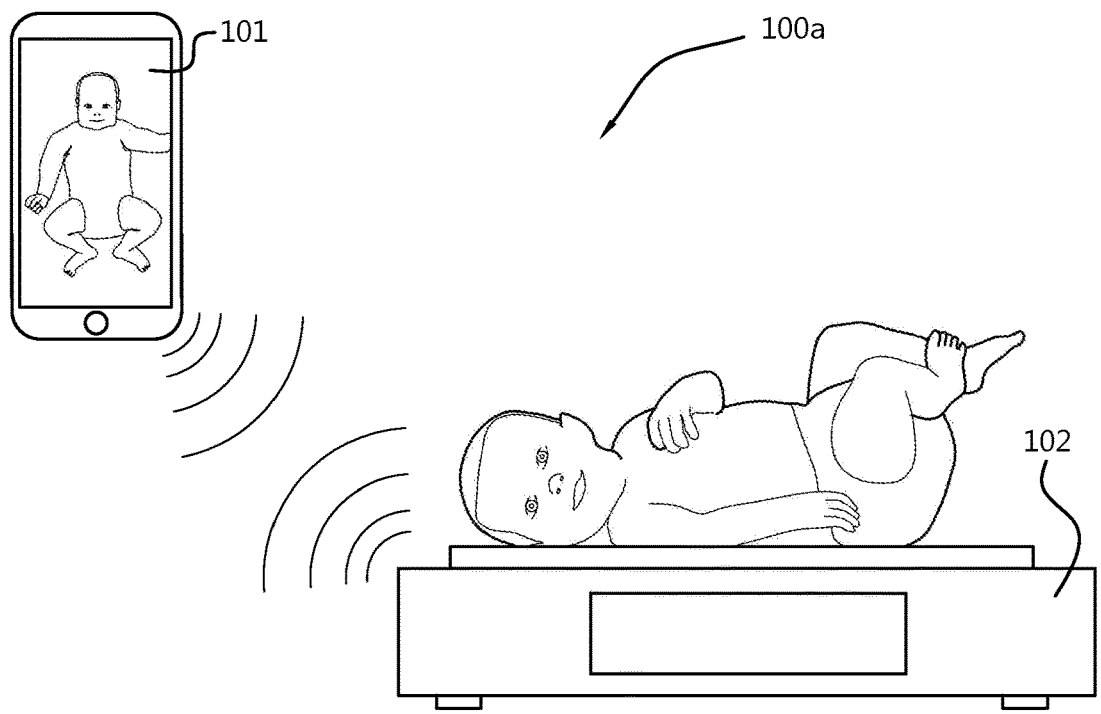
FIG. 1a schematically shows a system overview according to an embodiment of the present invention.

Different parameters are considered when tracking the development characteristics of a baby. Among the parameters for analyzing the development of a baby are its weight, its height and its head circumference.

Baby weighing scales are well-known devices that range from the basic models to the high-end ones that include Bluetooth transceivers, apps to be run in portable devices, and ergonomic designs.

Other weighing techniques include electronic technology with load cells or strain gauges, or weight measuring through air or liquid pressure.

Length measurement devices can also be found nowadays in different forms, starting from basic scales, to capacitive linear encoders wherein linear change in resistance makes length measurements possible, or other linear encoders such as optical, magnetic or inductive linear encoders. Ultrasound technology is also used, as well as kinect or laser 3D scanning technology, wherein the laser range finder finds the distance of a surface by timing the round-trip time of a pulse of light.

Pattern detection using a camera is also used for length measurement, wherein the measured product covers a surface with a pattern that is detected by the camera and which serves to calibrate the dimensions of the visual input of the camera. For example, the mat on which the baby lies can be provided with a distinct pattern to support the shape recognition algorithm and to calibrate dimensions. An image processing technique used for length measurement is body part and reference detection, wherein colour, contrast, shape, and other parameters can be detected by using algorithms and automatically labelling objects. Camera-driven apps are also used, wherein the app calibrates and calculates measurements of a photographed product based upon a reference object, as well as capacitive sensing technology wherein length is measured relative to a position on the screen of a (portable) device (such as iPhone, iPad).

For head circumference measurements, there are analogue technology devices such as measuring headbands that can be placed around the baby's head. There exist also more sophisticated devices like digital headbands or headbands with integrated (capacitive) linear encoding technology, or elastic headbands with (stretched) printed codes that can be captured by a camera, and by pattern calibration detection the measurement can be performed.

In the more sophisticated measuring devices, measurements can be transmitted to receiving devices, which can be portable devices such as mobile phones, tablets, or the like, wherein an app is being executed by the device's processor, and the received information is processed.

The communication between the measuring device and the app can take place using different communication technologies, such as Bluetooth, Wi-Fi, cabled connections, radio frequency identification (RFID), Infrared, code recognition by a touch screen, code or pattern recognition by a camera, or even manual input of the measured data.

In the following description, details will be provided about different embodiments that allow parents and caretakers to track the development and surrounding characteristics of their babies at any time using a portable device and different measuring devices.

FIG. 1a schematically shows a system overview 100a according to an embodiment of the present invention. In this embodiment, the weight and height of a baby are monitored. A user of a portable device 101, namely a parent or caretaker of the baby, captures an image of the baby lying on a mat. From this image, via an app running in the portable device and using reference points and image processing techniques, such as shape recognition techniques, the processor of the portable device can obtain information such as height and femur length of the baby, which can be stored in the portable device together with the captured image.

When the portable device 101 establishes a wireless connection with a weighing scale 102 that includes a transceiver, and on which the baby's mat is placed, the portable device can receive baby's weight information. The processor of the portable device then combines the information obtained from the captured image and the information obtained from the weighing scale, and it can generate and subsequently store development statistics of the baby. With the new statistics and the stored statistics, graphical development information can be displayed in the screen of the portable device so that the parents can monitor the development of their babies. Where needed, the measurements as taken can be assessed individually as well.

The portable device may already be connected to the weighing scale when the image is captured, or may establish a connection afterwards. Similarly, the weighing scale may send the weight information to the portable device immediately after the measurement is performed, or when requested by the portable device, this is, when the user of the portable device desires to establish a connection.

Additionally, the weighing scale may be included in a baby changing mat, so that the weight of the baby can be obtained and sent to the portable device, and then the baby can be changed there, with no need for an additional device where the baby has to lie in an uncomfortable position. The weighing scale may also be called weighing mat throughout the description.

Figure 1B:
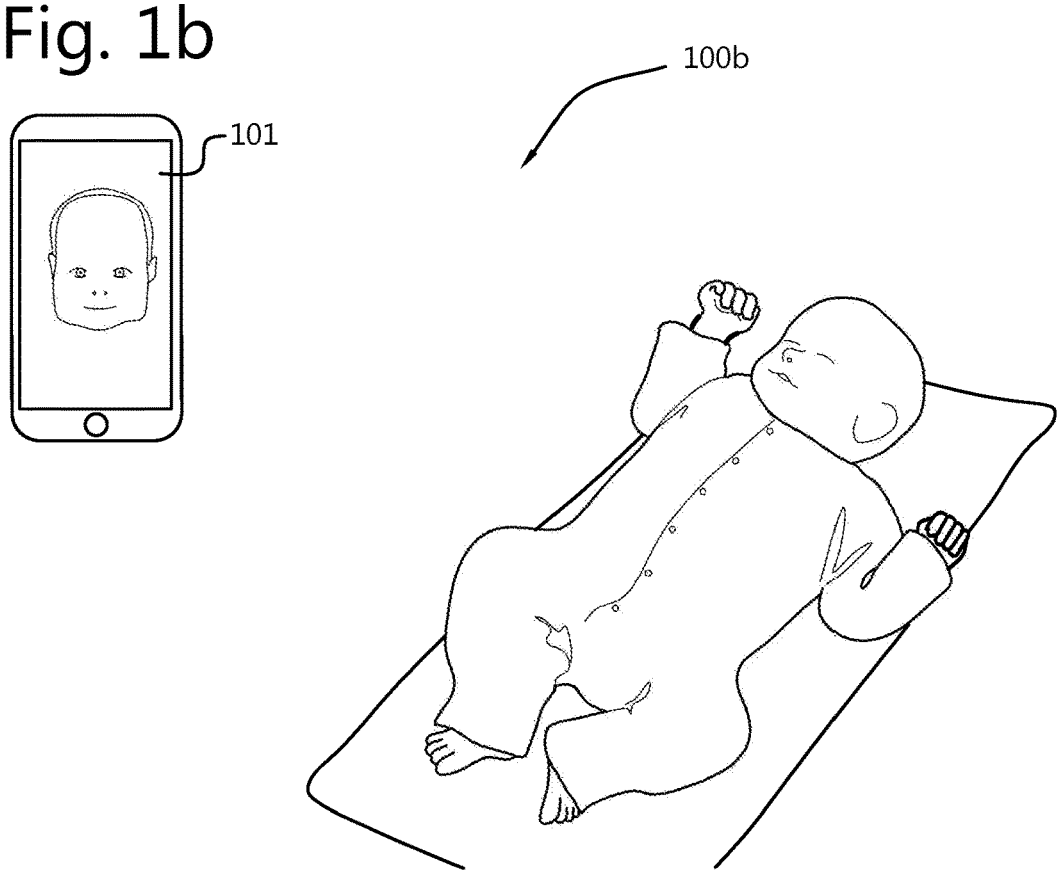
FIG. 1b shows a system overview according to another embodiment of the present invention.

FIG. 1b shows a system overview according to another embodiment of the present invention. In this embodiment, the development of the baby is monitored by measuring the height and the head circumference of the baby, and therefore there is no need to establish a connection with a weighing mat. For the height measurements, the portable device acts as in the embodiment of FIG. 1a, and the measured information is stored in the portable terminal.

The head circumference, also referred to as OFC (occipital frontal circumference) is measured over the most prominent part of the back of the head, known as the occiput, and above the eyebrows, known as the supraorbital ridges, conforming the largest circumference of the head.

The head circumference of the baby can be manually measured with a measuring device such as a measuring headband or the like, and the measured length can then be typed in the app in the portable terminal so that this information can also be used to obtain development statistics of the baby. The head circumference can also be measured by means of other measurement devices that can establish a connection with the portable terminal and send the information.

The head circumference can also be measured by means of visual information obtained with the portable device. One or multiple photos may be taken of the baby, or a movie, from different positions, such as from the form of the baby's head, from a side, and from the backside. Using known size references the processor of the portable device can use image processing techniques to calculate the head circumference.

In an embodiment according the invention, a photo of the baby lying facing up may be taken, wherein reference points in the mat allow for obtaining reference strips in the screen of the portable device that are used for calibration. Then, a photo of the baby lying on one side may be taken, also using reference points, and the information obtained from both photos can be combined by the processor of the portable device so that head circumference can be calculated.

With the new statistics and the stored statistics, graphical development information can be displayed in the screen of the portable device so that the parents and caretakers can monitor the development of their baby.

The present application is aimed at performing measurements on babies with ages from 0 to 24 months, preferably from 0 to 12 months or from 0 to 6 months. More preferably, the measurements should be taken on a baby whose development has not yet reached the stage in which it is able to walk. The invention is therefore directed to babies that are not able to stand or walk, and hence the most comfortable way to perform the measurements is by allowing the baby to lay down in a natural position.

The measurements performed may be extrapolated to infants of an age of 2 years to 20 years. Parents often wonder about the height that their child will reach when entering adulthood. This information can somewhat be extrapolated in a conventional manner from the measured patterns obtained in the present invention.

The app can be downloaded and is running in the portable device, for example on devices using iOS or Android as operating systems. It allows the processor to perform the necessary operations to obtain and provide the development statistics, and it may have several modes of operation. When initializing the app for the first time, by providing the birth date of the baby, the weight of the baby at birth and preferably its gender and/or nationality, a profile may be created and all the obtained information may be stored. More profiles can be created for more babies, such as for example a sibling whose development and surrounding characteristics the parents also want to monitor. When normally initializing the app, a profile is selected, and further options may be displayed, such as whether to see previously stored statistics, or to obtain new statistics. These statistics can be, among others, development statistics, condition statistics, or environment statistics. Additionally, different measuring devices can be selected from among those with a connection established with the portable device. For example, if the weighting mat is currently connected via a Bluetooth connection with the portable device, this device can be selected from among the menu options and measurements from it can be received. Then the portable device can stop the connection with the weighing mat and start a connection with another measuring device, by selecting the corresponding device from among those displayed in the menu. An advantage of providing the birthdate and gender of the infant is that proper comparisons can be made to growth curves of a vast number of normally developing, healthy infants in the best possible manner. A similar consideration applies to being able to enter the gender of the infant.

In the embodiments according the invention, the portable device is preferably connected to the weighing scale using a Bluetooth or Bluetooth Low Energy (LE) (hereafter: Bluetooth) connection. The portable device can also receive measuring information from other devices with which it can initiate a connection via Bluetooth. As such, the portable terminal can first be connected to the weighing mat or scale where the baby is lying, and then the portable device can switch and establish a connection with another device. In this way, in a single operation, the app can obtain development and additional information.

The information obtained from the captured images and the weighing scale may then be sent to a health database shared with the baby's healthcare provider (HCP), so that relevant information of the development of the baby is available to the HCP, and warnings can be sent to the portable device when the statistics obtained are close to a dangerous threshold or outside an expected range. Information stored in the portable device can be growth percentile information, so that the measurements performed on the baby can be compared with several percentiles, such as the $50^{th}$ percentile, that gives information about height and weight in average of babies of a specific age and gender. In a situation in which the values obtained are outside expected values, such as if the baby has overweight, underweight, or measurements suggest that the baby could soon have overweight or underweight, the baby can be taken to the HCP, and he will already have indicatory information that supports in knowing which further steps to take. This can be determined by the app by calculating the baby's body mass index (BMI) and comparing it with expected values for its age, length and gender.

Figure 2C:
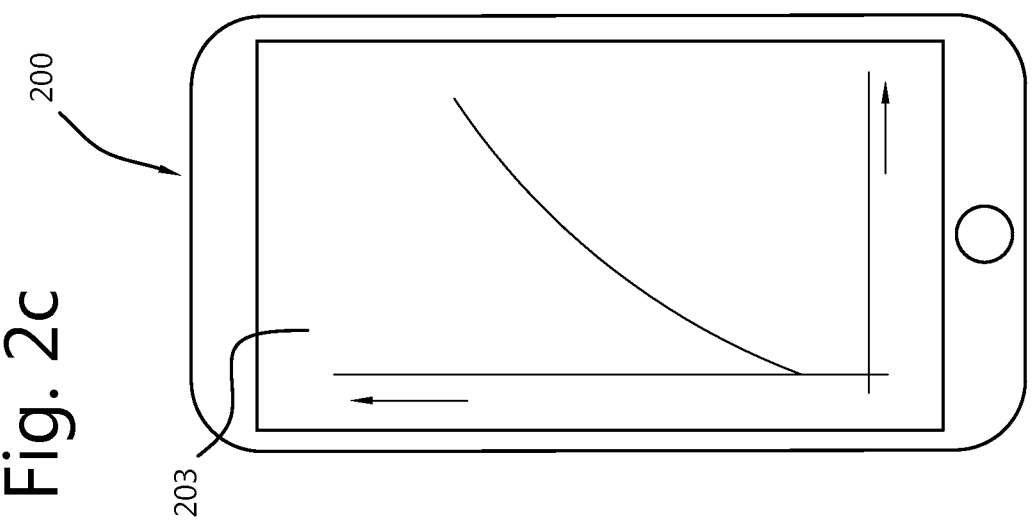
FIGS. 2a-c schematically illustrates screenshots of the portable device during different steps of the procedure according to an embodiment of the present invention.
Figure 2B:
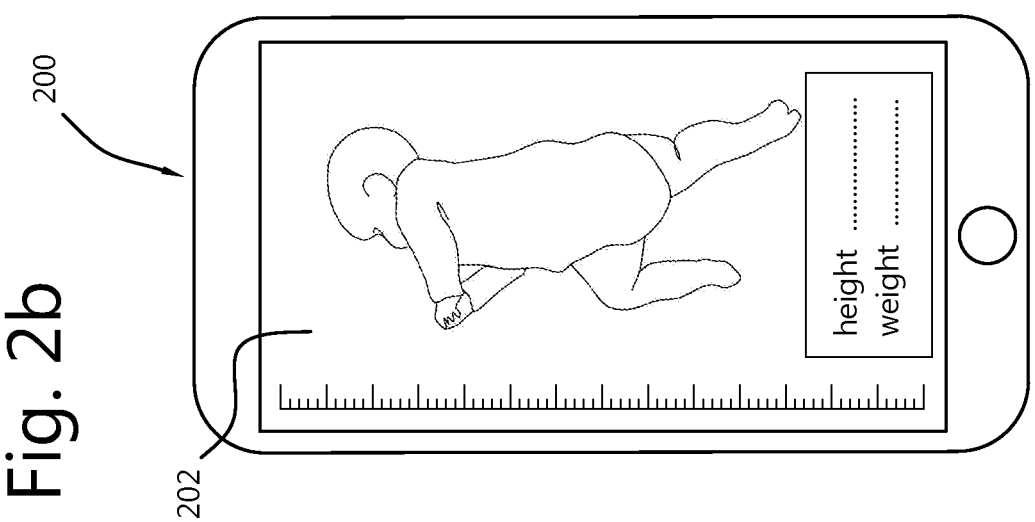
Figure 2A:
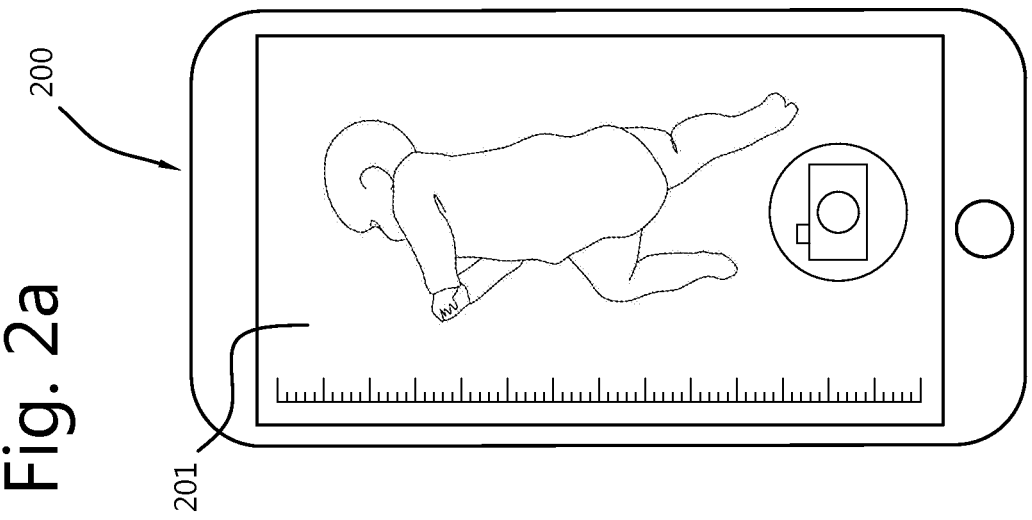
Figure 3A:
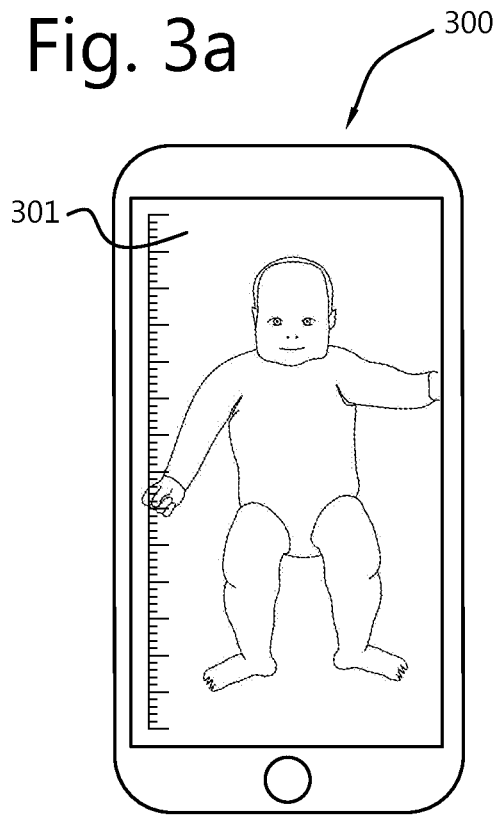
FIGS. 3a-d schematically shows screenshots of the portable device using shape recognition according to an embodiment of the present invention.
Figure 3B:
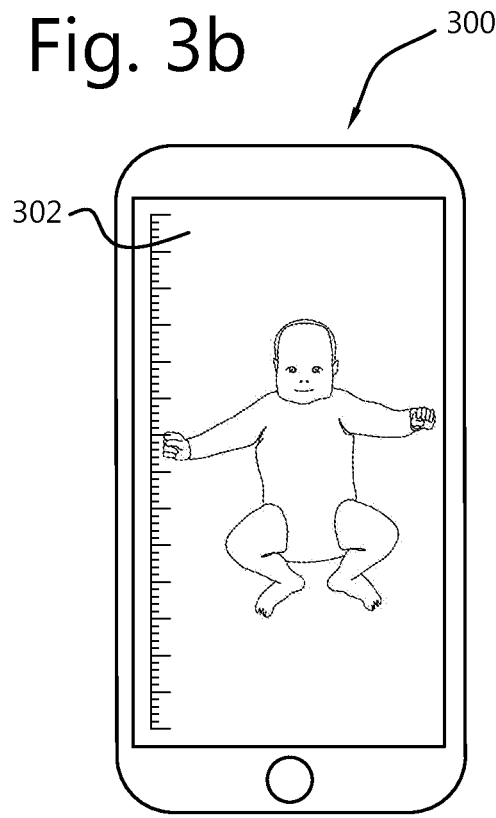
Figure 3C:
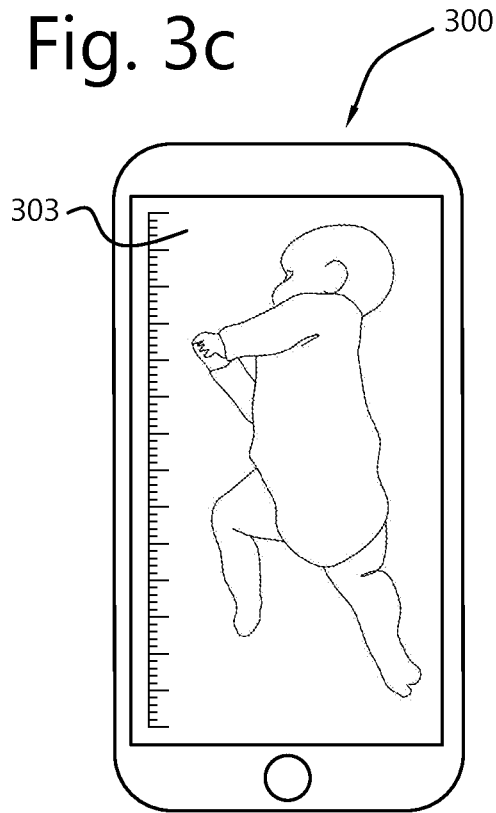
Figure 3D:
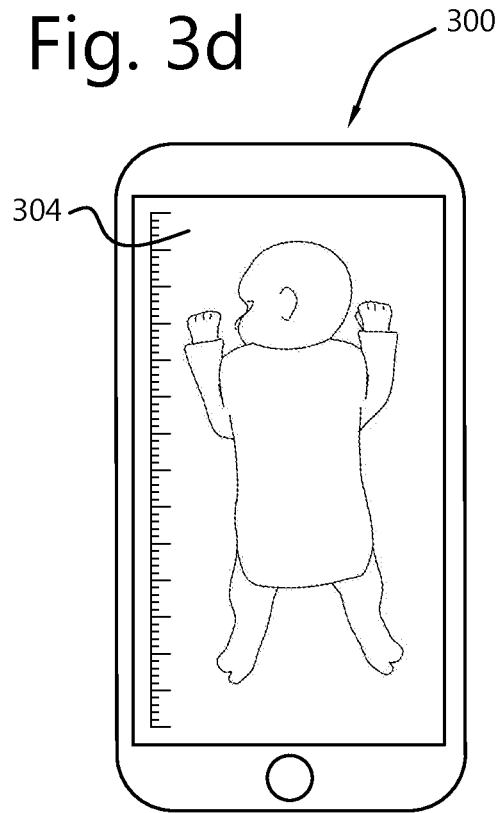

FIGS. 2a-c schematically show screenshots of the portable device during different steps of the procedure according to an embodiment of the present invention. If the app has entered the baby profile, a list of possible measurements may be displayed, and the parents can make the measurements that they desire. This list may comprise at least weight, height, abdominal perimeter and head circumference measurements. If the option of measuring height of the baby is selected, then the first step is to capture 201 an image of the baby. In order to perform this measurement in an optimal manner, it might only be necessary to slightly stretch the baby's legs in order to place them in the correct position according with the reference points. Since the baby is in a familiar environment, it is more likely that it will be calm and still, allowing for accurate measurements. By applying image processing techniques for shape recognition, the processor can obtain information 202 about the height of the baby, its femur length or the size of its head. This information is then stored in the portable device, together with the captured image.

If from the list of possible measurements, weight measurement is selected, then it is necessary that the portable device establishes a connection with the weighing scale. Once the connection is established and the baby is lying on the scale, weight information is received from the weighing scale 102, it is combined with the stored information and development statistics are calculated. Then these statistics are displayed 203 on the screen of the portable device, preferably in a graphical manner that allows for a quick and clear understanding. Here a comparison can be made both with previously stored development information, and with expected patterns and percentiles. The statistics may also be shared with a health database accessible by the baby's HCP, and also with social media services such as Facebook, Instagram, Twitter, WhatsApp or the like.

FIGS. 3a-d illustrate screenshots of the portable device using shape recognition according to an embodiment of the present invention. By using shape recognition techniques, information about the baby's height, femur length, the abdominal perimeter or head size can be obtained without the need to keep the baby still in an uncomfortable position with the legs straight. The baby can lie face up with his legs and arms straight 301, face up with his legs bended and his arms open 302, shrank sideways 303, face down 304, or in any other position.

Several shape recognition techniques may be used. In an embodiment according the invention, the portable device analyses a picture of the baby using known reference points or patterns printed on the scale or on a mat located over the scale. The portable device may have information about the distance between the reference points and it may compare the real distance with the distance in pixels. This provides the ratio of pixels and centimetres, so the portable device can perform the measurements in pixel units and then convert them to centimetres.

In another embodiment according the invention, the camera's ratio of the length in pixels and the real length may be pre-calculated, for different distances, and already known by the portable device. The portable device may measure the distance between the portable device and the surface where the baby lies when taking the picture. Once the picture is taken, the camera of the portable device may select the most appropriate value from among the stored ratios and applies it for calculating the measurement of the baby.

In another embodiment according the invention, before the first measurement is done, the user may place a ruler on the surface of the mat or the scale and take several pictures of the mat or scale from different distances from the ruler. For example, the user may take five photos from different distances. The portable device then may calculate the distance and read the ruler to calculate the ratios depending on the distance. The appropriate ratio is then used for the end calculation.

In yet another embodiment according the invention, a 3D model of a baby may be used. The portable device has information about the 3D model and, when the picture is taken, feature matching may be applied with the captured 2D image. The 3D model can be obtained with photogrammetry or stereo-photogrammetry techniques using the camera of the portable device.

FIG. 4 illustrates a process for tracking infant development statistics according to an embodiment of the present invention. When the option of obtaining height measurement is selected in the menu of the app, first an image of the baby is captured 401 with the camera of the portable device, using known size reference points, with which information such as the height or femur length of the baby is derived 402. The derived information is then stored 403 in the portable device, development statistics are obtained 404 by comparing the obtained measurement with predetermined patters or percentiles, and a development or growth graph is then displayed 405 representing the results obtained in an easy and user-friendly manner.

Figure 5:
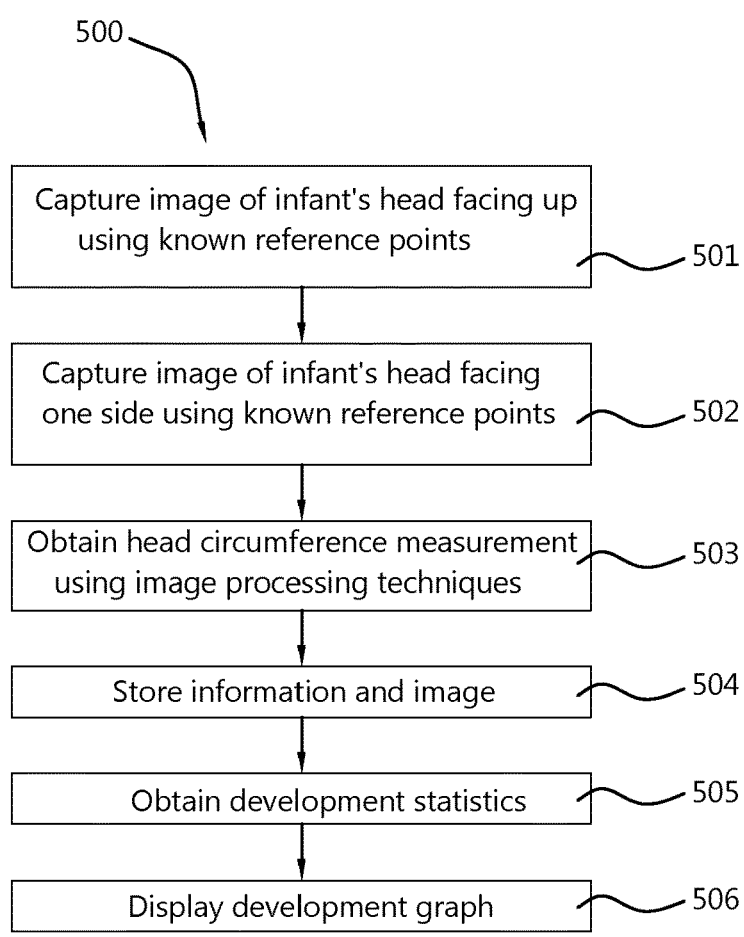
FIG. 5 illustrates a process for tracking infant development statistics according to another embodiment of the present invention.

FIG. 5 shows a process for tracking infant development statistics according to another embodiment of the present invention. When the option of obtaining a head circumference measurement is selected, one or multiple photos or videos of the baby's head are taken from different positions with the camera of the portable device. In an embodiment of the present invention, an image of the baby facing up is captured 501, using reference points located on the mat where the baby is lying, from which reference strips are generated in the screen of the portable device to calibrate the measurement. Afterwards, an image of the baby facing one side is captured 502, also using the same reference points. With these two measurements, the processor of the portable device can perform the necessary operations to obtain 503 the head circumference. It should be noted that the photos in different positions can be taken in a different order, which can be configured via for example a settings option in the app of the portable device, or via any other similar means. The obtained measurement is stored 504 in the portable device, this measurement is then used by the processor to obtain 505 development statistics of the baby, and then these statistics are displayed 506 on the screen of the portable device by means of a development or growth graph.

Figure 6:
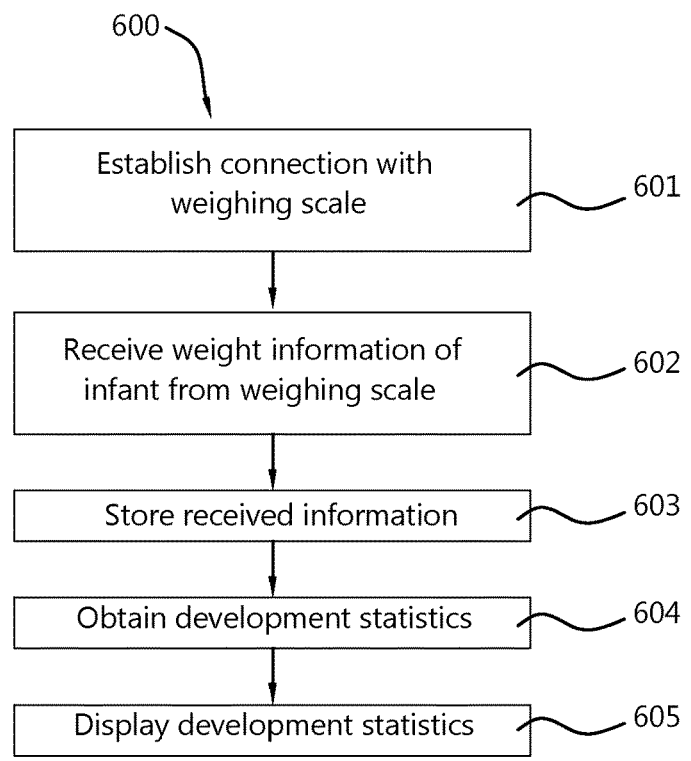
FIG. 6 illustrates a process for tracking infant development statistics according to another embodiment of the present invention.

FIG. 6 illustrates a process for tracking infant development statistics according to another embodiment of the present invention. If or when the device has established 601 a Bluetooth connection with the weighing scale, and the baby is lying on a mat on the weighing scale, the portable device receives 602 from the scale weight information. After that the processor of the portable device stores 603 the received weight information in the portable device, and obtains 604 development statistics. The statistics are displayed 605 on the screen of the portable device via for instance a growth or development graph. If desired, the statistics can then be shared on a database accessible by the baby's HCP, or the statistics graphs can be shared in social media services such as Facebook, Twitter, Instagram, WhatsApp, or the like.

It should be noted that the method steps above described do not need to be taken in the described specific order. This is, weight information can be received from the weighing scale and stored in the portable device, and the images can be captured afterwards. If the parents are only interested in obtaining height and head circumference measurements, it is not necessary that the weighing scale is connected to the portable device. Different types of measurements can be taken independently.

In all the embodiments of the invention, it can happen that one or more of the indicators analyzed presents a value that is close to a dangerous level, such as a development graph that deviates from the expected pattern, or that is not within an expected percentile for the age and gender of the baby.

The expected patterns or the safety levels within which some indicators must be can be stored in the portable device, and then the app itself generates a warning message or notification to the user indicating that one or more indicators are close to a dangerous level. This allows the parents or caretakers to know when to adjust accordingly or to take the baby to the HCP, if necessary.

If the calculated statistics are shared in the health database with the HCP, the portable device may receive the warning alarm from the database, and no expected patterns or safety range values have to be stored in the device. In this case, in case the baby is taken to the HPC, he already has the indicatory information about what symptoms the baby has.

In the foregoing description of the figures, the invention has been described with reference to specific embodiments thereof. It will, however, be evident that various modifications and changes may be made thereto without departing from the scope of the invention as summarized in the attached claims.

In particular, combinations of specific features of various aspects of the invention may be made. An aspect of the invention may be further advantageously enhanced by adding a feature that was described in relation to another aspect of the invention.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. A system for tracking infant development, the system comprising:
   (a) a portable device comprising a camera and a processor, and
   (b) a weighing scale;
   wherein the weighing scale is configured to measure the weight of an infant and to transmit measured weight information to the portable device; and
   wherein the portable device is configured to
      (i) capture an image of the infant;
      (ii) combine the measured weight information and information derived from the image of the infant to obtain infant development statistics; and
      (iii) store the image and the development statistics in a storage;
   wherein the information derived from the image comprises at least one of the height of the infant or the head circumference of the infant;
   wherein the infant development statistics are calculated by the portable device using shape recognition, and
   wherein the portable device is configured to capture the image of the infant when the infant is in any one of a plurality of positions.

2. The system of claim 1, wherein the weighing scale comprises a wireless transceiver.

3. The system of claim 1, wherein the portable device is further configured to obtain the infant development statistics from an infant between 0 and 24 months of age.

4. The system of claim 1, wherein the portable device is further configured to update previously stored infant development statistics relating to the same infant with the obtained infant development statistics.

5. The system of claim 4, wherein the portable device is configured to differentiate and track the development of at least one additional infant.

6. The system of claim 1, wherein a profile is created for the infant subject of the measurements, wherein at least birth date information and weight at birth information are provided, and wherein the profile is stored in the storage.

7. The system of claim 1, wherein the portable device and the weighing scale communicate via a wireless link.

8. The system of claim 1, wherein the infant development statistics are displayed on a display of the portable device in the form of a development graph.

9. The system of claim 1, wherein the portable device is further configured to receive measuring information from other devices.

10. The system according to claim 1, wherein an operating system of the portable device is one of IOS or Android, and wherein the portable device is a handheld device.

11. The system of claim 1, wherein the portable device is further configured to transmit the images and the infant development statistics to social media services servers.

12. The system of claim 1, wherein the measured weight information is sent to the portable device automatically every time a measurement is performed.

13. The system of claim 1, wherein the measured weight information is sent to the portable device when a request from the portable device is received.

14. The system of claim 1, wherein the weighing scale with the wireless transmitter is included in an infant changing mat.

15. The system of claim 1, wherein a warning is activated in the portable device responsive to a determination that any indicators or patterns are outside expected values or ranges.

16. A portable device comprising:
   (a) a camera for capturing images,
   (b) a processor for processing information;
   wherein the portable device is configured to:
      (i) capture at least one image of an infant,
      (ii) obtain infant development statistics from information derived from the at least one image, and
      (iii) store the image and the infant development statistics in a storage;
   wherein the information derived from the image includes at least one of the height of the infant or the head circumference of the infant;
   wherein the infant development statistics are calculated by the portable device using shape recognition;
   wherein a profile is created for the infant, and
   wherein the portable device is configured to capture the image of the infant when the infant is in any one of a plurality of positions.

17. The portable device of claim 16, wherein the portable device is further configured to wirelessly receive weight information from a weighing scale and to obtain development statistics based on the received information.

18. The portable device of claim 16, wherein the portable device is configured to update previously stored infant development statistics relating to the same infant with the obtained infant development statistics.

19. The portable device of claim 16, wherein the portable device is configured to differentiate and track the development of at least one additional infant.

20. The portable device of claim 16, wherein the portable device is further configured to receive measuring information from other devices.

21. The portable device of claim 16, wherein the portable device is further configured to transmit the development statistics.

22. An infant changing mat configured to support an infant during diaper changing for the infant, the changing mat comprising:
- a weighing scale, which comprises a transceiver, optionally a wireless transceiver, for communicating with a portable device according to claim 16, the weighing scale being configured to:
  - (a) measure the weight of an infant, and
  - (b) send the measured weight information to the portable device to facilitate obtaining infant development statistics by the portable device.

23. The infant changing mat of claim 22, wherein the measured weight information is sent to the portable device automatically every time a measurement is performed and/or when a request from the portable device is received.

24. A non-transitory computer readable medium comprising computer program instructions which, when executed on a portable device, cause the portable device to perform operations according to claim 16.

* * * * *